United States Patent [19]

Arold

[11] 4,212,822
[45] Jul. 15, 1980

[54] PREPARATION OF O-DIALKYLAMINOMETHYLPHENOLS

[75] Inventor: Hermann Arold, Wuppertal, Fed. Rep. of Germany

[73] Assignee: Bayer Atkiengesellschaft, Leverkusen, Fed. Rep. of Germany

[21] Appl. No.: 755,905

[22] Filed: Dec. 30, 1976

[30] Foreign Application Priority Data

Jan. 20, 1976 [DE] Fed. Rep. of Germany ....... 2601782

[51] Int. Cl.² .............................................. C07C 85/18
[52] U.S. Cl. ......................... 260/570.9; 260/326.5 R; 546/192
[58] Field of Search ..................... 260/570.9, 326.5 R; 546/192

[56] References Cited

U.S. PATENT DOCUMENTS

| 3,155,704 | 11/1964 | Knapp | 260/570.9 X |
| 3,969,409 | 7/1976 | Muyano et al. | 260/570.9 X |

*Primary Examiner*—Robert V. Hines
*Attorney, Agent, or Firm*—Sprung, Felfe, Horn, Lynch & Kramer

[57] ABSTRACT

In the preparation of an o-dialkylaminomethylphenol of the formula

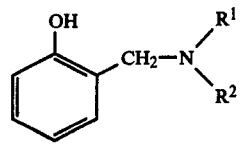

in which $R^1$ and $R^2$ each independently is alkyl with 1 to 6 carbon atoms, or $R^1$ and $R^2$ conjointly with the adjacent nitrogen atom, form a five-membered or six-membered ring, by reacting phenol, formaldehyde or paraformaldehyde and an amine of the formula

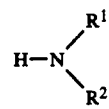

the improvement which comprises carrying out the reaction in the presence of an organic liquid which is immiscible with water but which is a solvent for the phenol and amine employed as starting materials and the o- dialkylaminomethylphenol which is formed.

Advantageously the amine is dimethylamine or diethylamine, the organic liquid is a member selected from the group consisting of cyclohexane, methylcyclohexane, methylene chloride, chloroform, carbon tetrachloride, ethylene chloride, diethyl ether, dipropyl ether, dibutyl ether, dipentyl ether, methyl butyl ether, ethyl propyl ether, diisopropyl ether and di-isobutyl ether, the reaction is effected at about 10° to 70° C., about 1.1 to 2 moles of phenol, about 1 mole of formaldehyde and about 2.5 to 3.5 moles of the organic liquid, after the reaction the by-product water is separated from the organic liquid containing the o-dialkylaminomethylphenol, the organic liquid is separated from the o-dialkylaminomethylphenol, and the organic liquid is recycled for further reaction.

11 Claims, No Drawings

PREPARATION OF O-DIALKYLAMINOMETHYLPHENOLS

The present invention relates to an unobvious process for the preparation of certain known o-dialkylaminomethylphenols, which can be used as intermediates for the synthesis of insecticidal active compounds.

It is already known that o-dialkylaminomethylphenols can be prepared by a "Mannich reaction" from phenol, a dialkylamine and formaldehyde or paraformaldehyde in water-miscible solvents, such as alcohols or dioxane, or in mixtures thereof with water, at reaction temperatures of between 20° and 80° C. (see H. Hellmann and G. Opitz, α-Aminoalkylierung (α-Aminoalkylation), page 140–142 (1960) Verlag Chemie, Weinheim, Bergstr.).

For example, o-dimethylaminomethylphenol is obtained in 43–50% yield by reaction of equimolar amounts of phenol and dimethylamine (as a 50% strength aqueous solution) with 40% strength aqueous formaldehyde solution, in ethanol as the solvent (see German Pat. No. 92,309 (1896) and A. Madinaveitia, Chem. Zentralbl. 1923 III, 915).

o-Diethylaminomethylphenol is obtained in 32–68% yield by reaction of equimolar amounts of phenol, diethylamine and approximately 40% strength aqueous formaldehyde solution [see J. H. Bruckhalter et al., J. Amer. chem. Soc. 68, 1894 (1946) and G. F. Grillot and W. T. Gormley, J. Amer. chem. Soc. 67, 1968 (1945)].

However, these processes display a number of disadvantages. Above all, isomers and homologues, for example bis- and tris-(dialkylaminomethyl)-phenols, and also polynuclear condendsation and resinification products are formed as by-products during the reaction.

Difficulties arise when these processes are carried out industrially, owing to the necessity for separation and disposal of the high-boiling and non-boiling by-products, listed above, which are obtained together with the o-dialkylaminomethyl phenol and most of which cannot be used industrially and have to be disposed of, which in some cases is possible only with the expenditure of a great deal of time and at a high cost.

Moreover, it has hitherto not been possible to obtain yields of more than 68%; as a rule the yields are 40%–50%. Furthermore, the aqueous solvents obtained during the reaction must be previously freed from water if they are to be reused, as is indispensible in the case of industrial processes. The industrial applicability of these processes is therefore restricted.

The present invention now provides a process for the preparation of an o-dialkylaminomethylphenol of the general formula

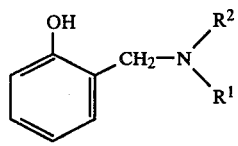

(I), in which $R^1$ and $R^2$ each independently is alkyl with 1 to 6 carbon atoms, or $R^1$ and $R^2$, conjointly with the adjacent nitrogen atom, form a five-membered or six-membered ring, from phenol, formaldehyde or a source thereof such as paraformaldehyde and an amine of the general formula

in which $R^1$ and $R^2$ have the abovementioned meanings, wherein the reaction is carried out in the presence of an organic solvent which is immiscible with water but which has the property of readily dissolving the phenol and amine employed as starting materials and the o-dialkylaminomethylphenol which is formed.

Preferably, $R^1$ and $R^2$ denote straight-chain or branched alkyl with 1 to 4 carbon atoms and especially with 1 to 3 carbon atoms.

It is to be regarded as extremely surprising that, under these reaction conditions, the desired o-dialkylaminomethyl-phenols are rapidly obtained in very high purity and high yields since, in view of the state of the art, it had to be expected that side reactions and, thus, relatively large amounts of by-products would certainly arise even when the reaction is carried out in water-immiscible solvents.

Compared with the known processes, the procedure according to the invention displays a number of advantages. Thus, a fact to be singled out above all is that, with the present procedure, the formation of condensation and resinification products is largely suppressed, as is also the formation of isomers and homologues, and as a result it is possible to raise the yields up to 96%.

A further advantage is that the water which is necessarily formed during the reaction can be separated off by simple phase separation and, thus, the solvent can easily be recycled into the reaction again without great difficulty. The unconverted phenol can, after recovery, also be fed back to the reaction.

If, for example, phenol, paraformaldehyde and dimethylamine are used as the starting materials, the course of the reaction can be represented by the following equation:

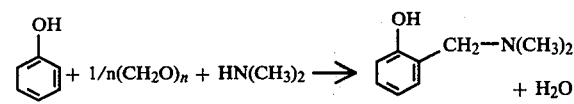

Phenol, which can be used according to the invention as a starting material, the amines (II) and also formaldehyde and paraformaldehyde are known and can be prepared readily, even on an industrial scale, according to methods known from the literature.

Solvents which can be used are hydrocarbons, which are liquid under the ambient conditions, such as cyclohexane or methylcyclohexane, aliphatic chlorinated hydrocarbons, such as methylene chloride, chloroform, carbon tetrachloride or ethylene chloride, and aliphatic dialkyl ethers, such as, for example, diethyl ether, dipropyl ether, dibutyl ether, dipentyl ether, methyl butyl ether, ethyl propyl ether and, preferably, diisopropyl ether and di-isobutyl ether.

When carrying out the process according to the invention about 1–5 moles of phenol, preferably about 1.1–2 moles of phenol, and about 1 mole of formaldehyde added as such or generated in situ from a precursor thereof such as paraformaldehyde in about 1–5 moles, and preferably about 2.5–3.5 moles, of a solvent, preferably a dialkyl ether, are employed per mole of the amine, preferably a dialkylamine, and especially dimethylamine or diethylamine, which amine is allowed to act on the mixture.

The reaction can be carried out at temperatures between about 0° and 110° C. The reaction can be carried out under normal pressure and also under elevated pressure.

The reaction is preferably carried out under normal pressure in closed or open vessels. The reaction is preferably carried out at temperatures of about 10°–70° C. The o-dialkylaminomethylphenol is isolated by separating off the water of reaction and then separating off and recycling the solvent and the excess phenol.

The dialkylaminophenols which can be prepared according to the process of the invention can be used as intermediates for the synthesis of plant protection agents, and especially of insecticidal active compounds, such as, for example, 2-(N-methylcarbamoyl)-benzyl ethyl thioether as described in German Published Specification DOS No. 1,910,588.

The process of the present invention is illustrated by the following preparative Examples.

EXAMPLE 1

0.4 kg of dimethylamine was passed, under normal pressure and at a reaction temperature of 20°–25° C., in the course of 5 hours into a mixture of 1.1 kg of phenol, 0.26 kg of paraformaldehyde and 3.1 kg of diisopropyl ether, as the solvent, while stirring, and the reaction mixture was then warmed to 60° C. for 1 hour. After cooling to room temperature, the water of reaction which had separated out was separated off.

After distilling off the ether, 1.605 kg of a mixture which, according to determination by gas chromatography, contained 0.264 kg of phenol, 1.23 kg of o-dimethylaminomethyl phenol, 0.017 kg of p-dimethylaminomethylphenol, 0.082 kg of 2,4- and 2,6-bis-dimethylaminomethylphenol and 0.012 kg of 2,4,6-tris-dimethylaminomethylphenol, were obtained and 1.21 kg (90% of theory, relative to converted phenol) of o-dimethylaminomethylphenol could be obtaind from this mixture by conventional methods of working up.

EXAMPLE 2

The procedure was as described in Example 1, but the phenol and paraformaldehyde in diisopropyl ether were reacted at 50° C. in separate runs with (a) 0.65 kg of diethylamine, (b) 0.632 kg pyrrolidine and (c) 0.90 kg of dipropylamine. Under the same reaction conditions and isolation conditions, 1.49 kg (about 93% of theory, relative to converted phenol) of o-diethylaminomethylphenol, 1.77 kg (about 96% of theory, relative to converted phenol) of o-dipropylaminomethylphenol and 1.50 kg (about 95% of theory, relative to converted phenol) of o-hydroxy-N-benzylpyrrolidine were obtained in (a), (b) and (c) respectively.

EXAMPLE 3

By effecting the process under the same conditions as in Example 1, but with the following solvents: (a) 3.1 kg of dibutyl ether, (b) 3.1 kg of methyl tert.-butyl ether and (c) 3.1 kg of diethyl ether, the following yields were obtained: (a) 1.14 kg (about 85% of theory) of o-dimethylaminomethylphenol, (b) 1.21 kg (about 90% of theory) of o-dimethylaminomethylphenol and (c) 1.19 kg (about 89% of theory) of o-dimethylaminomethylphenol.

EXAMPLE 4

By effecting the process under the same conditions as in Example 1, but with the following solvents: (a) 4.5 kg of cyclohexane and (b) 5.0 kg of chloroform, the following yields were obtained: (a) 1.09 kg (about 81% of theory) of o-dimethylaminomethylphenol and (b) 1.05 kg (about 78% of theory) of o-dimethylaminomethylphenol.

For comparison, the examples which follow were carried out using the solvents which are known to be used according to the prior art.

Comparative Example I 0.45 kg of dimethylamine was passed, under normal pressure and at a reaction temperature of 20°–25° C., in the course of 5 hours into a mixture of 1.0 kg of phenol, 0.30 kg of paraformaldehyde and 3.1 kg of methanol and the reaction mixture was then warmed to 60° C. for 1 hour. After distilling off methanol and water in vacuo, 1.551 kg of a mixture which contained 0.242 kg of phenol, 0.605 kg of o-dimethylaminomethylphenol, 0.030 kg of p-dimethylaminomethylphenol, 0.302 kg of bis- and tris-dimethylaminomethylphenol and 0.392 kg of condensation and resinification products was obtained and 0.595 kg (49% of theory, relative to converted phenol), of o-dimethylaminomethylphenol could be obtained from this mixture.

Comparative Example II

By effecting the process under the same conditions as in Comparative Example I, but using the following solvents: (a) 3.1 kg of ethanol and (b) 3.1 kg of dioxane, the following yields were obtained: (a) 0.610 kg (about 51% of theory) of o-dimethylaminomethylphenol and (b) 0.613 kg (about 51.5% of theory) of o-dimethylaminomethylphenol.

What we claim is:

1. In the preparation of an o-dialkylaminomethylphenol of the formula

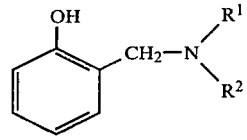

in which $R^1$ and $R^2$ each independently is alkyl with 1 to 6 carbon atoms, or $R^1$ and $R^2$ conjointly with the adjacent nitrogen atom, form a five-membered or six-membered ring, by reacting phenol, formaldehyde or paraformaldehyde and an amine of the formula

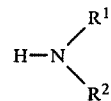

the improvement which comprises carrying out the reaction in the presence of an organic liquid which is immiscible with water but which is a solvent for the phenol and amine employed as starting materials and the o-dialkylaminomethylphenol which is formed.

2. The process according to claim 1, wherein the organic liquid is a dialkyl ether.

3. The process according to claim 2, wherein the ether is diisopropyl ether or diisobutyl ether.

4. The process according to claim 1, wherein the organic liquid is a hydrocarbon or aliphatic chlorinated hydrocarbon.

5. The process according to claim 1, wherein the reaction is effected at about 0° to 110° C.

6. The process according to claim 5, wherein the reaction is effected at about 10° to 70° C.

7. The process according to claim 1, wherein about 1 to 5 moles of phenol, about 1 mole of formaldehyde and about 1 to 5 moles of the organic liquid are employed per mole of the amine.

8. The process according to claim 1, wherein $R^1$ and $R^2$ each independently is alkyl of 1 to 4 carbon atoms.

9. The process according to claim 8, wherein $R^1$ and $R^2$ each independently is alkyl of 1 to 3 carbon atoms.

10. The process according to claim 9, wherein the amine is dimethylamine or diethylamine.

11. The process according to claim 10, wherein the organic liquid is a member selected from the group consisting of cyclohexane, methylcyclohexane, methylene chloride, chloroform, carbon tetrachloride, ethylene chloride, diethyl ether, dipropyl ether, dibutyl ether, dipentyl ether, methyl butyl ether, ethyl propyl ether, diisopropyl ether and di-isobutyl ether, the reaction is effected at about 10° to 70° C., about 1.1 to 2 moles of phenol, about 1 mole of formaldehyde and about 2.5 to 3.5 moles of the organic liquid, after the reaction the by-product water is separated from the organic liquid containing the o-dialkylaminomethylphenol, the organic liquid is separated from the o-dialkylaminomethylphenol, and the organic liquid is recycled for further reaction.

* * * * *